United States Patent [19]

Gunn

[11] 4,372,904
[45] Feb. 8, 1983

[54] METHOD FOR MAKING AN EAR PLUG

[76] Inventor: Dennis L. Gunn, P.O. Box 738, Atlanta, Tex. 75551

[21] Appl. No.: 248,562

[22] Filed: Mar. 27, 1981

Related U.S. Application Data

[63] Continuation of Ser. No. 813,009, Jul. 7, 1977, abandoned.

[51] Int. Cl.³ .................. B29C 5/00; B29C 17/10; B29D 3/00
[52] U.S. Cl. .................................. 264/134; 264/132; 264/161; 264/213; 264/221; 264/222; 264/279.1
[58] Field of Search .................. 264/16–20, 264/161, 213, 129, 134, 132, 222, 221, 317, 279.1; 427/4

[56] References Cited

U.S. PATENT DOCUMENTS

| | | | |
|---|---|---|---|
| 1,755,775 | 4/1930 | Dunn | 264/222 |
| 2,473,723 | 6/1949 | Nelson | 264/222 |
| 2,475,802 | 7/1949 | Osserman | 264/222 |
| 2,496,170 | 1/1950 | Mann | 264/221 |
| 2,528,219 | 10/1950 | Feagin | 264/317 |
| 3,097,059 | 7/1963 | Hoffman | 264/222 |
| 3,328,502 | 6/1967 | Robson | 264/279.1 |
| 3,440,314 | 4/1969 | Gordon | 264/222 |
| 3,638,709 | 2/1972 | Brown et al. | 427/4 |

FOREIGN PATENT DOCUMENTS 8960 of 1914 United Kingdom ................ 128/152

OTHER PUBLICATIONS

Schwartz, "Acrylic Plastics in Dentistry", Dental Items of Interest Pub. Co., N.Y., (1950), pp. 154–155.

Primary Examiner—Willard E. Hoag
Attorney, Agent, or Firm—Gunn, Lee & Jackson

[57] ABSTRACT

Method for making a coded, resilient ear plug including forming an impression with wax and release agent, investing the impression, agitating to remove air, hardening the investment and after removal of the impression material casting a hardenable material in the investment cavity.

1 Claim, 3 Drawing Figures

METHOD FOR MAKING AN EAR PLUG

This is a continuation of application Ser. No. 813,009, filed July 7, 1977 and now abandoned.

BACKGROUND OF THE DISCLOSURE

In industrial work areas, noise levels are sufficiently high that damage to the hearing of a worker may occur. The damage sometimes is very gradual, apparently being cumulative and sometime requiring years before the damage is noticeable. The damage occurs substantially without pain. As a consequence, many workmen gradually become deaf as a result of working in noisy environments. This deafness may be broad band across the entire audio spectrum. Other employees may lose substantial hearing at selected frequencies in the frequency range corresponding to the human voice.

Numerous earplugs have been devised in the past. It is believed that they have met with only limited success. The success has been primarily limited by the difficulty of fabrication. It is possible to make uniform or identically molded earplugs, but they do not uniformly fit the users. Users simply have different physical shapes, whether the earplug fits in the external ear or fits in some other fashion to the wearer and user. Mass produced uniformly made earplugs are generally not acceptable. To the extent that they are comfortable and fit well for some users, they are highly uncomfortable and fit very poorly with many other users. In this light, they will, in fact, either be ineffective or will be discarded if sufficiently discomforting.

The earplug of the present invention is a relatively simple device in retrospect. In this sense, it provides a radical change from the larger and cumbersome devices heretofore used. Moreover, it is a device that can be readily fitted to a large plant where scores, indeed hundreds, of workmen require individually fitted earplugs.

The present invention yields a product which is made from a cool impression of each ear of each individual user. Moreover, the attenuation may be adjusted to meet the noise level requirements of each user. The earplug which is made hereby has a substantially indefinite life and is not affected by the normal temperature excursions experienced by workmen. It typically does not require a coating or subsequent recoating as do some competitive devices. It is easily kept clean by daily washings with ordinary soap and water. Cleaning is easily achieved with boiling water. The device is believed to be substantially safer because it fits primarily in the ear canal only and not the outer ear. It can be attached by means of a long cord, exposed, and thus running from ear to ear so that supervisory personnel can readily observe a large work area with many workmen. This helps avoid discarding the ear protective devices which so many workmen do out of rebelliousness or resentment to the devices. The provision of a comfortable fit goes a long way in cutting down their resentment.

All of this is accomplished through the earplug of the present invention and the method for manufacturing disclosed herein.

The method of the present invention yields an improved earplug. This method results in the manufacture of an improved earplug. The earplug of the present invention is substantially improved in manufacturing over the earplug disclosed in the patent of Hocks, et al., U.S. Pat. No. 2,881,759. The device of Hocks is substantially worn in the external ear. The patent of French, U.S. Pat. No. 3,169,523, is directed to an external ear device. It is primarily on the exterior and is substantially exposed. The patent of Johnson, et al., U.S. Pat. No. 3,833,701, is substantially in the exterior ear. Moreover, the Johnson patent discloses a method of manufacture which is molded in situ. This is particularly set forth in multiple steps recited at Column 7 of that disclosure.

By contrast to these references, the method of the present invention yields a mass produced earplug which is substantially worn on the interior, not in the external ear.

The present apparatus and method for manufacturing yields an earplug which provides significant reduced sound levels in the critical frequency range of 1,000–8,000 Hertz. Reductions in the range of 30 db attenuation has been easily achieved with a vented version and more than 40 db attenuation with a nonvented version.

The present invention is a method of manufacturing which particularly lends itself to use in large plants where hundreds of employees must be individually measured and receive individually fabricated earplugs. By contrast, the present invention overcomes the shortcomings of the Johnson reference where attenuation is improved using a multiple number of dips (forming different or multiple layers) of a coated sealant placed on a base member. Johnson requires stretching of the external ear. It results in the fabrication of an earplug with an external handle which is not required. An external handle or projecting member is potentially dangerous from lateral impact to the head. The same exposure to lateral impact is found in the French reference.

DETAILED DESCRIPTION OF THE PRESENT INVENTION

Figure 1:
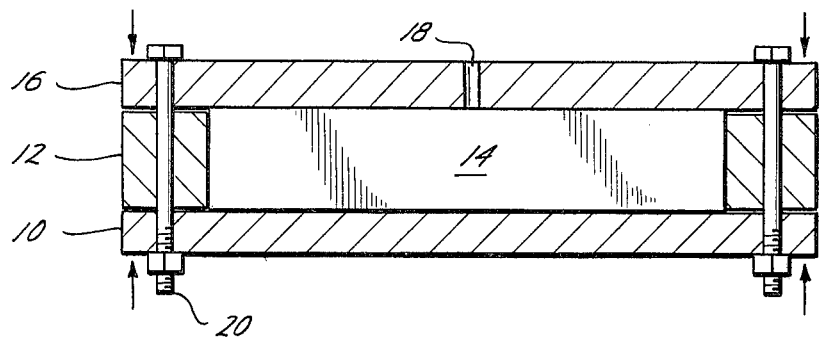
FIG. 1 is a sectional view through a mold apparatus for making earplugs.

This invention is directed to a method of manufacture for an earplug. The method of manufacture will be first stated, and, thereafter, the product will be described. The method of manufacture presumes that earplugs are to be made for a user who has two ears, both to be protected, and it further contemplates an individual of very average or normal physical circumstances. Notwithstanding this presumption, the present invention can be used with individuals with prior hearing loss, physical adnormalities of the ear, such as scar tissue, and the like. After the method has been stated, the product so manufactured will be described. It is believed that this order of disclosure is most efficient.

For a prospective user, an impression is first made. To this end, a cotton pellet which serves as a dam is placed in the ear canal. This causes some flaring in the final product which is desirable. To get this flare, the plug is inserted into the ear canal past the second bend, approximately one-half of the distance between the beginning of the ear canal and the eardrum. The cotton pellet should be relatively small. It should not be so large as to touch the eardrum, because this is very annoying to the user being fitted. The pellet is large enough that it will hold its position in the ear canal.

The next step requires the making of an impression in the ear canal. The impression is made by a polymer or copolymer. A good two-part copolymer system is provided by Coe Laboratories, which sells two parts to be mixed together. The two parts are sold under the trademark "Audalin." The Audalin comes in a powder which includes polyethyl methacrylate, coloring pigments and zinc undecylinate. A liquid curing agent which causes polymerization is typically used. It incorporates alkyl methacrylates, alkoxy alkyl acetate and suitable plasticizers. Instructions for the use of this impression material can be obtained from the source of the material. The impression material is characterized in that it is convenient to be used, comfortable to the user, does not require heating above body temperature so that a cure can be achieved at a comfortable temperature, cures in a reasonable interval determined by the amount of catalyst placed therein, and other scale factors which are not critical. Audalin is normally free of dermatological and allergenic problems. The finished product after the impression has cured is a mold shaped to the form of the ear canal. It is pliant and able to be removed from the ear canal by simple hand removal. Dental floss or other fine thread can be knotted to the cotton and used as a means of retrieval.

Impressions from many workers can be taken or can only be taken from a single user. In any event, the impression which is made of the ear is then removed to laboratory circumstances. Preferably it is made with some excess material in the external ear for ease of removal. At the lab, it is trimmed to remove that part of the impression obtained from the external ear. This leaves the canal portion. Additionally, it leaves a slight part which is exposed to a viewer only when that viewer is looking into the ear canal. So to speak, an outer face is formed which is, in a typical adult, smaller than the size of a dime. This portion is provided for ease of handling and ease of guidance of the canal portion into the ear. It does not lock into the outer ear.

After the impression has been obtained and trimmed, it is dipped in liquid dental wax. The dental wax is typically heated to about 150° F. This coats the impression, and it is dried. This can be accomplished at room temperature and typically without regard to the humidity. After the dental wax has dried, the coated impression is dipped in soapy water which serves to free the impression from the casting which will be described. The soapy water serves as a parting agent.

Under the assumption that many are to be made simultaneously, but certainly not as a limitation on the present invention in the manufacture of a single earpiece, the impression is placed on a flask. As the term is used in this disclosure, the flask is characterized in that it will support a number of impressions. It is further characterized in that it is flat or planar, has a surface which is number coded to identify each impression, and serves as a base plate.

The next step in the manufacture of the ear mold of the present invention is the step of gluing, through the use of putty or some sacrificial glue, the impression to the flask. The glue or adhesive is applied at the end of the impression which was on the exterior of the ear. It will be recalled that substantially all of the impression which was in the external ear was previously trimmed away. This leaves a more or less flat face. This flat face is suitable for gluing to the flask.

The flask is next submerged in unset dental stone. This is mixed to a consistency approximately equal to a milk shake, typically having a consistency which pours more readily than honey but with more difficulty than water. To this end, the flask is surrounded by a removable mold wall. This will be described in detail hereinafter.

After the dental stone has been poured on the flask and has completely submerged the impressions to a substantial depth (about one inch), typically two or three times deeper than the height of the impression, it is tapped to cause bubbles to float to the surface. Tapping will suffice. The use of a vibrator imparting vibrations to the flask will also suffice. This vibration or tapping continues for perhaps one minute or until all the bubbles have been substantially floated to the surface.

FIG. 1 shows a pressurized mold arrangement. The flask 10 serves as a base, while a surrounding mold border 12 encases the liquid dental stone 14 placed on the interior. A top plate 16 having a weephole 18 is forced against the liquid dental stone, and pressure is applied. Any surplus of liquid overflows. When pressure is applied, as by the use of a C-clamp and the weight of the plate 16, the excess dental stone flows from the hole 18. The plate 10 is numerically marked and subdivided so many plugs can be made simultaneously without confusing them.

The dental stone is permitted to harden. Thereafter, the mold of FIG. 1 is disassembled. It will be recalled that the impressions are on the bottom of the cured dental stone 14. Accordingly, the bottom plate 10 is removed. This exposes at the bottom face the pliable impressions. It will be recalled that they were held in place by a suitable adhesive. When the flask 10 is removed, the adhesive seal is broken. The pliable impressions are exposed at that face of the dental stone and are removed.

The dental stone is then visually inspected, and, with a knife, sharp corners at the multiple cavities formed by the impressions are trimmed. The term "cavity" refers to the opening formed in the dental stone 14 by the impression which was adhesively joined to the flask 10.

After the sharp corners are trimmed, an air jet is used to blow dust from the dental stone 14. The dental stone thus then forms an investment cavity mold which enables the next steps in the procedure.

The next step in the operation is to pour onto the top face of the dental stone 14 (the bottom face as shown in FIG. 1) a coating material. It is a tin foil substitute. It has the viscosity of thirty weight lubricating oil. One suitable source is Coe-Sep, which is manufactured by the previously identified Coe Laboratories. The entire face is coated. The Coe-Sep coating material coats the porous dental stone. The dental stone is similar in texture to sandstone. To this extent, it has a slightly rough surface. The dental stone is a bit too granular at its surface which is smoothed by the coating material poured onto it. An excess is splashed onto the surface to assure one hundred percent coverage. The coverage extends into the investment cavities formed in the dental stone 14. Any surplus is poured off. Thereafter, the coating material is permitted to dry.

The next step in the procedure is to mix and prepare a substantial quantity of a copolymer for the investment cavities. A suitable material is sold under the brand name "Audalin." As previously mentioned, it is a two-part polymer system utilizing polyethyl methacrylate. The liquid part is a suitable catalyst and plasticizer. Other polymer materials are acceptable provided they form a similar earplug. The unset copolymer is mixed and stirred until it has the consistency of dough, and it is packed into the investment cavity. It is thoroughly packed, and a surplus is accumulated on the surface. Surplus builds up slightly above the investment cavity opening. At this juncture, the flask 10 is restored to its position against the mold border 12 and the dental stone 14. Substantial pressure is applied to the device. The pressure is applied by using a C-clamp, hydraulic jack or other equipment. A pressure in the range of about sixty pounds per square inch is applied in the direction of the arrows indicated in FIG. 1. As an example, about four thousand pounds force are applied over about seventy-two square inches of surface area. When this is done, any surplus copolymer will be squeezed from the cavity and will squirt out around the edges of the flask 10. So that the forces can be handled quite easily, the flask 10 is preferably a substantial steel plate. A thickness of one-half to five-eighths inches will suffice. The mold border or frame 12 is also a heavy steel plate having a thickness of up to about five-eighths inches. The top plate 16 is of similar construction.

After pressure is maintained for a short period, typically about two minutes, the flask 10 is then removed. The unset copolymer which has not yet cured is visually inspected for bubbles. It has a puttylike consistency. The investment cavity is repacked at this juncture by applying additional uncured copolymer. The flask 10 is repositioned and repressurized for approximately the same pressure and interval mentioned above. The sequence is repeated at least once, typically two or three times. It is repeated until the bubbles in the investment cavities are squeezed out.

The flask plate 10, the frame or mold border 12 and the top plate 16 are assembled with nuts and stud bolts 20 which clamp the entire assembly together.

An annealing step next occurs. The clamped flask and other equipment shown in FIG. 1 of the drawings is then placed under water for temperature stabilization. The particular temperature is dependent on the type and mix of copolymer used. The temperature chosen is the temperature specified by the manufacturer of the copolymer. It will be observed that Audalin is only one copolymer system available. Others can be used. It specifies a particular curing temperature. The temperature of the water cures the copolymer. After the appropriate temperature has been applied for a specified interval, the assembled apparatus of FIG. 1 is removed from the heat soak bath and permitted to cool slowly to room temperature. The flask 10 is removed. Then, the dental stone 14 is broken so that a break runs through each investment cavity. The cast earplug is removed from the investment cavity at the break. It is visually inspected for void, discolorations, bubbles, surface flaws and the like. As needed, it can be touched up to some extent by handwork using a grinder, such as polishing with wet pumice on a polishing lathe.

As desired, the earplug is coded for purposes of identification using numbers on the flask 10 or color coding. It will be recalled that it has an outer face which was reasonably flat, being defined by the flask 10, where a hole can be drilled. Using a very small drill, a very small hole is drilled, typically not even one-fourth of an inch deep. Through the use of a syringe, a colored polymer is injected into the hole. The color marking enables a user to identify the right from left. Other coding marks can be used to distinguish the earplugs of one worker from another.

Figure 2:
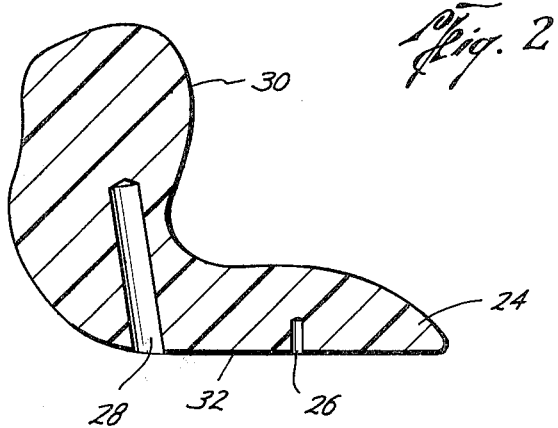
FIG. 2 is a side view of a completed earplug.

A completed plug is shown in FIG. 2 of the drawings. The plug is identified by the numeral 24. The color marking is shown at 26 to denote a specific plug. Another hole is drilled at 28. A string of suitable size, color and type is dipped in an uncured adhesive and is placed in the drilled hole 28. It is permitted to cure and form a string which attaches one earplug to another. The string is some suitable length so that it can hang around the neck of the user. A suitable industrial glue will serve to join the string to the earplug 24.

The completed earplug formed of Audalin or another polymer is a pliant but firm structure which holds the shape required for the use contemplated for it. The earplug is nonporous. That is to say, it is a closed cell copolymer body. This prevents absorption of bacteria. It is not necessary to polish, coat or otherwise protect the surface of the earplug 24. It is nonallergenic. It does not have any dermatological impact. It does not absorb sweat. It is easily cleaned by dipping in boiling water. It can thus be worn indefinitely in the ear. It can be worn quite easily for the entire work day without discomfort. In particular, it will be observed that the earplug, when installed in the ear, is shaped to the ear canal. The number 30 identifies the innermost end. This end portion is positioned in the ear canal just beyond the second bend, it being recalled that the plug of cotton was positioned at that location. The outer face 32 can be seen by looking directly into the ear canal of the wearer. However, that part of the earplug is substantially recessed so that it is not supported by the outer ear. In other words, the earplug is relatively short. Because it is short, it positions very little material in the outer ear and, indeed, does not use any kind of wedging or clamping action in attachment to the outer ear. The weight is light as to be negligible.

The physical characteristics of the cured earpiece are preferably in the following ranges. Upon the application of finger pressure, the unconfined cast copolymer has a resilient yield in the range of about two to about ten percent. It gives in all directions and responds to shearing force in like manner. It has memory and is thus restored to its original shape as long as pressures found in normal handling and usage are not exceeded.

The earplug 24 can be optionally drilled all the way through. A suitable vent hole can be formed in it by drilling from the base 32 to the opposite end. The hole which is placed in it can range from as small as one-thirty-second of an inch to as large as one-sixteenth of an inch diameter. This reduces the attenuation of the earplug. As an example, this permits a user to talk on the telephone without removing the earplug. The vent hole is optional, and its omission seems to provide substantially more attenuation.

Before curing, the polymeric material optionally is mixed with an antibacterial agent. The addition of a small percentage serves as an antiallergenic material and does not alter curing or physical characteristics. Coloring agents can be mixed in. Other additives can be mixed in the polymer before curing.

Figure 3:
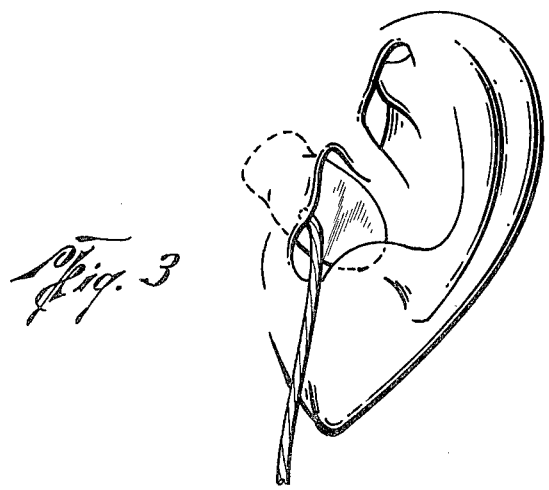
FIG. 3 shows the present earplug in the ear of a user.

The physical dimensions and shape variations are dependent on the shape of the user. Nevertheless, within the constraints of this disclosure, the inventive earplug 24 is primarily devoid of external ear structure. The view of FIG. 3 shows the earplug fitted into the ear canal and further depicts how it avoids engagement with the outer ear.

The foregoing sets forth the preferred embodiment, but the scope thereof is determined by the claims.

I claim:

1. A method for forming an earplug for reduction of noise when worn by a user which method comprises the steps of:
   (a) first placing a fibrous pellet in the ear canal of a user past the second bend and thereafter forming a plastic impression of the ear adjacent to the pellet, and wherein some excess plastic impression is formed which excess is partly shaped by the external ear and which reaches the outer end of the ear canal;
   (b) trimming the plastic impression to form a generally flat face thereon which trimming removes the external ear portion of the impression;
   (c) coating the trimmed impression with an external wax coating by dipping, and dipping the impression in a soapy liquid parting agent and thereafter permitting the impression to dry at room temperature and thereby harden on the outer surface;
   (d) glueing the trimmed impression along with a plurality of similarly obtained impressions to a flask plate at the flat face thereon;
   (e) placing a dam means around the flask plate and pouring a liquid which cures into a stonelike material over the flask plate to a depth sufficient to submerge and fully surround the plastic impression;
   (f) agitating the flask plate and liquid to cause air bubbles to rise to the top of the liquid;
   (g) curing the liquid to form a stonelike solid member;
   (h) removing the flask plate from the solid member and thereafter removing the plastic impressions to leave investment cavities therein and trimming said investment to remove any sharp corners formed therein;
   (i) coating the solid member and walls defining said investment cavities formed therein with a liquid mold release material to enhance subsequent mold release and permitting the liquid to dry;
   (j) placing a liquid material which is capable of curing into a solid resilient material in the cavities including the steps of:
      (1) making a first pour of liquid material;
      (2) pressure packing the first pour of liquid material;
      (3) making a second pour of liquid material after the first while the first pour is still liquid;
      (4) pressure packing the second pour of liquid material;
      (5) repeating steps (1) to (4) until the investment cavities are filled with uncured liquid material free of voids and bubbles;
   (k) pressure curing the uncured liquid material at a temperature elevated sufficiently to obtain curing thereof into a resilient material;
   (l) reducing the temperature to a level permitting access to the cured resilient earplug material;
   (m) breaking the solid member across the cavity to remove the cured earplug; and
   (n) coding the cured earplug to facilitate the identification of a left earplug from a right earplug using number or color coding.

* * * * *